United States Patent [19]

Theeuwes

[11] 4,278,087
[45] Jul. 14, 1981

[54] DEVICE WITH INTEGRATED OPERATIONS FOR CONTROLLING RELEASE OF AGENT

[75] Inventor: Felix Theeuwes, Los Altos, Calif.

[73] Assignee: Alza Corporation, Palo Alto, Calif.

[21] Appl. No.: 144,211

[22] Filed: Apr. 28, 1980

[51] Int. Cl.³ .............................................. A61M 7/00
[52] U.S. Cl. ................................................. 128/260
[58] Field of Search ...................... 128/127, 130, 260; 424/19, 22

[56] References Cited

U.S. PATENT DOCUMENTS

| | | | |
|---|---|---|---|
| 4,036,228 | 7/1977 | Theeuwes | 128/260 |
| 4,177,256 | 12/1979 | Michaels et al. | 128/260 |
| 4,217,898 | 8/1980 | Theeuwes | 128/260 |

Primary Examiner—C. Fred Rosenbaum
Attorney, Agent, or Firm—Edward L. Mandell; Paul L. Sabatine

[57] ABSTRACT

An osmotic device is disclosed for delivering an agent to an environment of use. The device comprises (1) a semipermeable wall, surrounding a compartment with a passageway through the wall for delivering an agent from the compartment, and (2) an osmotic system in the compartment comprising a body formed of a polymer having depots consisting of an agent osmotic solute dispersed in the polymer and surrounded individually by a layer of the polymer. In operation, agent is delivered by the device imbibing fluid from the environment through the semipermeable wall into the compartment, with the system imbibing fluid from the compartment into the depots dissolving the solute and filling the depots with solution, thereby causing the depots to form apertures and release agent, with (a) the system delivering the agent at a controlled rate to the compartment and (b) the device delivering the agent from the compartment at a controlled rate through the passageway to the exterior of the device.

9 Claims, 6 Drawing Figures

DEVICE WITH INTEGRATED OPERATIONS FOR CONTROLLING RELEASE OF AGENT

FIELD OF THE INVENTION

This invention pertains to an osmotic device for the controlled delivery of an agent. The device provides a preprogrammed, unattended delivery of agent at a controlled rate, and for a time period, established to meet a specific need. The device is manufactured for delivering the agent to environments of use, including drug receptor environments.

BACKGROUND OF THE INVENTION

Osmotic devices manufactured for delivering useful agents are known to the prior art in U.S. Pat. Nos. 3,845,770 and 3,916,899, both issued to Theeuwes and Higuchi. The devices disclosed in these patents are made with a wall formed of a material that is permeable to an exterior fluid and substantially impermeable to the passage of agent. The wall surrounds a compartment that contains an agent. The device delivers the agent through a passageway in the wall to the exterior of the device. Osmotic delivery systems embracing a different structure and mode of operation also are known to the prior art in U.S. Pat. No. 4,177,256, issued to Michaels and Guillod. The systems disclosed in this patent consists of depots of drug particles dispersed in and surrounded by a polymer. The systems releases drug by depots rupturing to deliver drug to the exterior of the system. The manufactures of these patents are remarkably effective for delivering many agents to different environments of use.

While the above inventions represent significant and pioneering advancements in the delivery art, and while they are useful for dispensing numerous agents, there is an occasional instance where the delivery of an agent may require more control than is provided by prior art for its delivery to the environment of use. For example, if the agent is very soluble in fluid imbibed into the compartment, or in a separate operation the agent is very soluble in fluid imbibed into the depots, the agent in either instance may be delivered individually at a high rate and in an amount in excess of that required for obtaining a preselected result. In the light of the above presentation, it will be appreciated by those versed in the art, that if a delivery device is made available that integrates and simultaneously uses the physical and chemical embodiments of the prior art device and system, in a single unit device for enhanced control of the delivery of agents, such a device would have a positive value and also represents an unexpected advancement in the art.

OBJECTS OF THE INVENTION

Accordingly, it is an immediate object of this invention to provide a novel delivery device for the controlled and continuous delivery of an active agent over a prolonged period of time, which device represents a significant improvement over the prior art.

Another object of the invention is to provide a useful delivery device designed with a minimum number of parts and having improved control over the delivery of agent from the device.

Another object of the invention is to provide a delivery device comprising cooperating parts that act in concert as a single unit device for a more controlled delivery of a beneficial agent.

Still another object of the invention is to provide an osmotic device for dispensing useful agents that because of their intrinsic properties, are difficult to dispense, and which agents can be dispensed by the device of this invention at a controlled and continuous rate for performing their intended effects.

Still a further object of the invention is to provide an osmotic delivery device that can administer a complete pharmaceutical regimen at a controlled rate and for a particular time period, the use of which requires intervention only for initiation and possibly termination of the regimen.

Yet a further object of this invention is to provide an osmotic delivery device that maintains its integrity, arising from its physical structure, while in the environment of use, and which delivers an active agent at a controlled and continuous rate over a prolonged period of time.

Still a further object of this invention is to provide an osmotic device comprising an exterior wall having various thickness supported by an interior osmotic polymeric system.

Still a further object of this invention is to provide an osmotic device that delivers the active agent in a dilute solution from the device over time.

Other objects, features and advantages of this invention will be more apparent to those skilled in the art from the following detailed specification taken in conjunction with the drawings and the accompanying claims.

SUMMARY OF THE INVENTION

This invention concerns an osmotic delivery device for dispensing an agent to an environment of use. The device comprises a pair of osmotic releasing means for delivering the agent at a controlled rate over a prolonged period of time.

BRIEF DESCRIPTION OF THE DRAWINGS

In the drawings, which are not drawn to scale, but are set forth to illustrate the invention, the Figures are as follows.

In the drawings, and the specification-like parts in related Figures are identified by like numbers. The terms appearing earlier in the specification and in the description of the drawings, as well as embodiments thereof, are further described elsewhere in the disclosure.

DETAILED DESCRIPTION OF THE DRAWINGS

Figure 1:
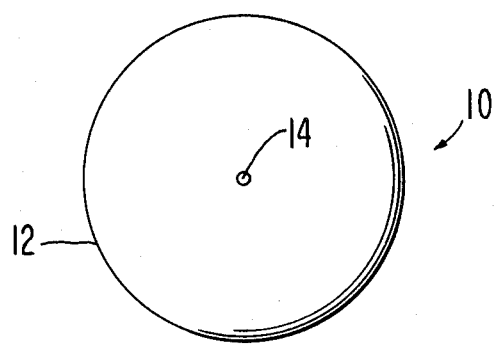
FIG. 1 is a top view of an osmotic device designed and manufactured for delivering a beneficial agent.

Turning now to the drawings in detail, which are examples of an osmotic device of the invention, and which examples are not to be construed as limiting, one embodiment of a device is indicated in FIG. 1 by the numeral 10. In FIG. 1, device 10 is seen in a top view, and it comprises a wall 12 and a passageway 14.

Figure 2:
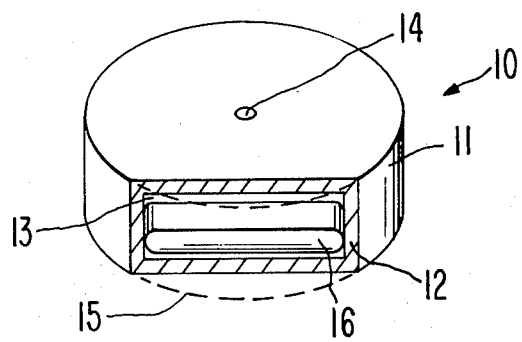
FIG. 2 is a side view of the osmotic device of FIG. 1, in opened section with a part of the wall of the device removed for illustrating the interior compartment of the device.

Referring to FIG. 2, device 10 of FIG. 1 is seen in opened section at 15. As seen in FIG. 2, device 10 comprises a body 11 which body comprises a wall 12 that surrounds and defines a compartment 13. A passageway 14 in wall 12 connects compartment 13 with the exterior of device 10. Compartment 13 houses an osmotic system 16, described in FIG. 3. Open section 15 is formed by removing a section of wall 12. Wall 12 is formed of a synthetic or naturally occurring semi-permeable material, and a detailed description of these materials appears later in the specification.

Figure 3:
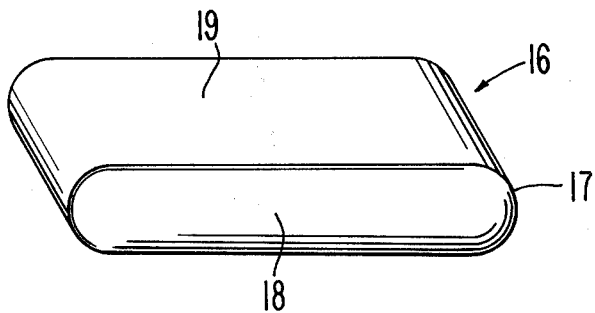
FIG. 3 is a view of the osmotic system housed in the compartment of the device as seen in FIGS. 1 and 2.

FIG. 3 is an enlarged view of the osmotic system 16 as seen in compartment 13 of FIG. 2. System 16 comprises a body 17 made of film 18 consisting essentially of a single, solid polymer, and system 16 has at least one surface 19 for releasing an agent, not shown in FIG. 3, to the exterior of system 16, in this embodiment compartment 13. System 16 is manufactured in any shape that is sized and adapted for placement in compartment 13.

Figure 4:
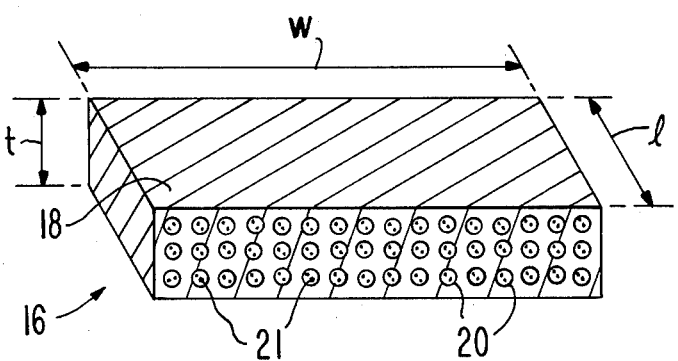
FIG. 4 is the total osmotic system seen in isolation, with its top and sides sections away for depicting the interior structure of the system.
Figure 5:
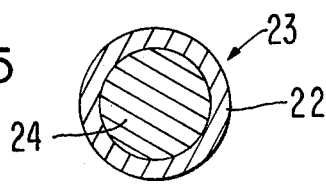
FIG. 5 represents an isolated depot as taken from FIG. 4, which depot is illustrated as a spherical osmotic capsule consisting of an osmotically active particle core encapsulated with a semipermeable membrane; and, FIG. 6 is a graph depicting the rate of release from a measured and a calculated osmotic system.

System 16 of FIG. 3 is seen in FIG. 4 with its top and sides cut away for depicting the internal structure of system 16. In FIG. 4, osmotic system 16 comprises a plurality of discrete depots 20 of agent 21, represented by dots, dispersed throughout body 17, a polymer matrix. The polymer surrounds and encapsulates depots 20, and it binds them into a solid unit body 17. The polymer surrounds depots 20 individually so that each depot 20 is encapsulated by a layer of polymer. In FIG. 5, a depot 23 is presented as a single depot, isolated from the multiplicity of depots comprising system 16. A detailed disclosure pertaining to the structure and the operation of FIG. 5 is presented later in the specification. The polymer comprising system 16 is made of a material that is non-toxic, substantially non-erodible in the environment of use, it is substantially impermeable to the passage of agent 21, and it is permeable to the passage of an external fluid that enters compartment 13. Agent 21 is present in depots 20 as the osmotically effective solute, usually as the salt of agent 21.

Device 10, in operation in the environment of use releases agent 21 by a combined, integrated operation of device 10 and system 16. Device 10 operates by imbibing fluid into compartment 13 in a tendency towards osmotic equilibrium at a rate determined by the permeability of wall 12 and the osmotic pressure gradient across wall 12, to continuously dissolve agent 21 in compartment 13 that is osmotically pumped from device 10 through passageway 14 to the exterior of device 10. System 16, in compartment 13 operates in harmony with device 10 by fluid diffusing into system 16 from compartment 13, and then into depots 20 dissolving agent 21 therein. The rate of fluid imbibition into depots 20 is related to the osmotic pressure gradient exhibited by agent 21 across the polymer encapsulating depot 20 against fluid in compartment 13. As fluid is imbibed into depots 20, it continuously dissolves agent solute 21 and continuously fills depots 20 with solution, thereby generating a hydrostatic pressure in depot 20. This pressure is applied against the polymer causing it to rupture and form an aperture. Agent 21 is then released through the aperture from depot 20 near the surface of system 16 to compartment 13. Agent 21 is released continuously from system 16 by the inward progressive formation of apertures in depot 20, forming a lattice of dispensing paths in system 16 for releasing agent 21 from within system 16. The dispensing paths can form openings on all sides of system 16, and they can be interconnected through paths of regular and irregular shapes discernible by microscopic examination. As fluid is imbibed into depots 20, it fills the paths and they become a means for transporting agent therethrough, with release occurring at a controlled and beneficial rate to compartment 13. Device 10, operating in unity with system 16 which device 10 osmotically pumps agent 21 released by system 16 to the exterior of the device 10.

While FIGS. 1 through 5 are illustrative of various devices that can be made according to the invention, it is understood these devices are not to be construed as limiting, as the devices can take a wide variety of shapes, sizes and forms for delivering agents to different environments of use. For example, the devices include buccal, vaginal, implants, pessaries, artificial glands, uterine and eye devices. The devices made for oral use can have various conventional shapes and sizes such as round with a diameter of 3/16 inches to ½ inches, or it can be shaped like a capsule having a range of sizes from triple zero to zero, and from 1 to 8. The device also can be adapted for delivering an active agent in streams, aquariums, fields, factories, reservoirs, laboratory facilities, hot houses, transportation means, hospitals, clinics, nursing homes, and other environments of use.

DETAILED DESCRIPTION OF THE INVENTION

In accordance with the practice of this invention, device 10 is manufactured with a wall 12 formed of a material that does not adversely affect agent 21, an animal body, or the environment of use, and it is permeable to an external fluid such as water and biological fluids, while substantially impermeable to agents and the like. The selectively permeable materials forming wall 12 are insoluble in body fluids, and they keep their integrity during operation of device 10. Typical materials for forming wall 12 include materials know to the art as semipermeable polymers, such as cellulose acrylate, cellulose diacylate, cellulose triacylate, cellulose acetate, cellulose diacetate, cellulose triacetate, semipermeable polyamides, semipermeable polyurethanes, semipermeable sulfonated polystyrenes, semipermeable ionically associated polymers, and the like. The polymers are disclosed in U.S. Pat. Nos. 3,845,770; 3,916,899; 4,034,758; and 4,111,203.

The expression passageway, 14, as used herein denotes an orifice, bore, hole or the like through wall 12 of device 10. The passageway can be formed by mechanical drilling, laser drilling, or by eroding an erodible element, such as a gelatin plug in wall 12, in the environment of use. A detailed description of osmotic passageways, and the maximum and the minimum dimensions of passageways is disclosed in U.S. Pat. Nos. 3,845,770 and 3,916,899.

Device 10 is manufactured by standard techniques. For example, wall 12 is formed in one presently preferred procedure by an air suspension procedure. This procedure consists in suspending and tumbling osmotic system 16 in a current of air and a wall forming polymer mixed with a fluid carrier to form wall 12 surrounding and defining compartment 13 housing system 16. The air suspension procedure is described in U.S. Pat. Nos. 2,799,241; in *J. Am. Pharm. Assoc.,* Vol. 48, pp. 451-459, 1959; and ibid., Vol. 49, pp. 82-84, 1960. Other wall forming techniques such as pan coating can be used in which the materials are deposited by successive spraying of a polymer solution, or tumbling in a rotating pan. Other standard manufacturing procedures are described in *Modern Plastics Encyclopedia,* Vol. 46, pages 62-70 1969; and in *Pharmaceutical Sciences,* by Remington, 14th Ed., pages 1626-1678, 1970, published by Mack Publishing Company, Easton, Penna.

Osmotic system 16, housed in compartment 13, is made from polymeric materials, comprising a plurality of discret depots 20 of agent solute 21 dispersed throughout the polymeric material. A layer of the polymeric material surrounds and encloses the agent solute as depots, and binds them into a solid system 16. The polymer comprising the system surrounds the depots of agent solute individually, so that each depot is encapsulated by a layer of polymer as illustrated in FIGS. 4 and 5. The polymer comprising system 16 is impermeable to the passage of agent solute, and it is permeable to the passage of external fluid presence in compartment 13.

The osmotic system 16 houses from about 0.5 to 80 weight-percent of agent solute, with the remaining weight percent polymer. Generally, the depots are about 2 to 50 percent by weight, with a more preferred range of 5 to 40% by weight of the system. The amount of agent solute released from system 16 to device 10 will be about 10 nanograms to 50 milligrams per hour, or higher. The system will release solute over a prolonged period of 4 hours to 30 days, or longer.

Generally, the agent solute will have a particle size of 0.1 to 1000 microns, and a presently preferred particle size of about 0.5 to 300 microns, average. Procedures for measuring the surface area average diameter of agent solutes are reported in *J. Am. Chem. Soc.* Vol. 6, page 309, 1938; *The Surface Chemistry of Solids,* by Gregg, 2nd Ed., 1961 published by Reinhold Corp., New York, in *Absorption, Surface Area and Porosity,* by Gregg et al., 1967 published by Academic Press, New York, in *Physical Absorption of Gases,* by Yound et al., 1962, published by Butterworth and Company, Ltd., London; and in *Find Particle Measurements,* by Valla, 1959, published by Macmillan Co., New York.

Polymer materials suitable for manufacturing system 16 can be selected from naturally occurring and synthetic polymeric materials. These polymers are compatible with the agent solute, they can form the encapsulating layer of the depot, they are substantially impermeable to the passage of drug solute, they are permeable to the passage of water and fluid in compartment 13, they are nonerodible, they do not dissolve in water and biological fluids, and they form an aperture during operation of the system in the device. Procedure for a ascertaining the impermeability and the permeability of polymeric films are known to the art in *Proc. Roy. Sci.* London, Series A, Vol. 148, 1935; *J. Pharm. Sci.* Vol. 55, pages 1224-1229, 1966; in *Diffusion in Solids, Liquids and Gases,* by Jost, Chapter XI, pages 436-488, 1960, published by Academic Press, Inc., New York. Procedures for measuring aperture formation in system 16 formed by the hydrostatic pressure in the depots exceeding the cohesive integrity of the polymer, with the polymer opening for releasing solute to compartment 13, can be determined by measurements predicted on pressure-deflection and mechanical behavior measurement techniques reported in *Modern Plastics,* Vol. 41, pages 143-144, 146 and 186, 1964; *Handbook of Common Polymers,* by Scott et al., pages 588-609, 1971; published by CRC Press, Cleveland, Ohio; in *Machine Design,* pages 107-111, 1975; in *J. Sci. Instruments,* Vol. 42, pages 591-596, 1965; and by measuring mechanical stress-strain patterns of polymers using the Instron ® Testing Machine, available from the Instron Corporation of Canton, Massachusetts. The osmotic pressure, expressed as ATM, of agent solutes can be measured in a commercially available osmometer that measures the vapor pressure difference between pure water and the solution containing a solute to be analyzed, and according to standard thermodynamic principles, the vapor pressure ratio is converted into osmotic pressure difference. An osmometer that can be used for the present measurements is identified as Model 302 B Vapor pressure osmometer, manufactured by the Hewlett Packard Company, Avondale, Pa.

Exemplary polymers for fabricating system 16 include ethylene-vinyl ester copolymers having an ester content of 4 to 80% such as ethylene-vinyl acetate copolymer, ethylene-vinyl hexanoate copolymer, ethylene-vinyl butyrate copolymer, ethylene-vinyl pentantoate copolymer, ethylene-vinyl trimethyl acetate copolymer, ethylene-vinyl diethyl acetate copolymer, ethylene-vinyl 3-methyl butanoate copolymer, ethylene-vinyl 3,3-dimethyl butanoate copolymer and ethylene-vinyl benzoate copolymer. Additional exemplary materials suitable for manufacturing system 16 include acrylonitrile-methyl vinyl ether, vinyl chloride-diethyl fumarate, homopolymers and copolymers of partially hydrolyzed poly(vinyl), plasticized poly(vinyl chloride), plasticized poly(amides), poly(isoprene), poly(isobutylene), poly(ethylene), lightly cross-linked polyvinyl pyrrolidone), vinyl-diethyl fumarate copolymers, ethylene-propylene copolymers, poly(urethanes), plasticized cellulose esters and ethers, and the like. The polymeric materials are known in *Handbook of Common Polymers,* by Scott, et all, Sections 1 through 42, 1971, published by CRC Press, Cleveland, Ohio, and in U.S. Pat. No. 4,177,256.

The term agent as used herein includes any compound that can be delivered from device 10 to produce an intended result. The term agent include pesticides, herbicides, biocides, algicides, rodenticides, insecticides, anti-oxidants, catalysts, chemical reactants, nutrients, drugs, and the like. The term also includes an inert agent, in which embodiment, the device pumps fluid as a driving source for powering articles of manufacture connected to the osmotic device.

In presently preferred embodiment, the term agent include drug solutes. The term drug include hypnotics, sedative, psychic energizers, tranquilizers, anticonvulsants, muscle relaxants, analgesics, anti-inflammatory agents, anesthetics, antispasmodics, anti-ulcer, antimicrobials, cardiovascular, diuretics, anti-neoplastics, antiviral, and the like. Typical drugs include ephedrine hydrochloride, ephedrine sulfate, isoproterenol hydrochloride, holinecarbamyl chloride, methscopolamine nitrate, alverine citrate, chlorphenoxamine hydrochloride, gentamicin sulfate, neomycin sulfate, potassium chloride, ferrous lactate, ferrous gluconate, sodium lactate and the like. The amount of drug in the system is a dosage unit amount for carrying out the desired therapy. The therapeutically effective amounts of drugs are known in the disclosed references. The drugs are known to the art in *Remington's Pharmaceutical Sciences,* 14th Ed., 1970, published by Mack *Pharmaceutical Sciences,* 14th Ed., 1970, published by Mack Publishing Co., Easton, Penna; and in *The Pharmacological Basis of Therapeutics,* by Goodman and Gilman, 4th Ed., 1970, published by the Macmillian Company, London.

DESCRIPTION OF EXAMPLES OF THE INVENTION

The following examples are merely illustrative of the present invention and they should not be considered as limiting the scope of the invention in any way, as these examples and other equivalents thereof will come more apparent to those versed in the art in the light of the present disclosure and the accompanying claims.

EXAMPLE 1

An osmotic system 16 for housing in compartment 13 of an osmotic device 10 is manufactured as follows: A 7 gram portion of micronized pilocarpine nitrate is admixed with 3 grams of an ethylene-vinyl acetate copolymer having an vinyl acetate content of 40%, and a melt index of 45–70 g/min. This copolymer has a tensile strength of about 600–700 psi, and an elongation at break of 1400% to 1500%. The copolymer is impermeable to pilocarpine nitrate, but it is permeable to water. Pilocarpine nitrate is a water-soluble drug and it functions as an osmotically effective solute. The pilocarpine nitrate particles are on the average about 40 microns in diameter. This mixture is heated to 120° C. and cast into a 6 mm thick film. A number of 9.5 mm sections, suitable for housing in the compartment are cut from the film, to form osmotic system 16.

Next, the systems are coated with a semipermeable membrane consisting of cellulose acetate having an acetyl content of 32%, by using the Wurster air suspension technique. A 5% polymer solution in acetone is used to apply the semipermeable wall. The wall has a thickness of about 5 mils. The devices are dried for 1 week at 50° C. to remove residual solvent. An aperture is made through the semipermeable wall of each device with a high speed drill to connect the comparment with the exterior of the device. The aperture had a diameter of about 7 mils. The device releases a therapeutically effective amount of the drug by the combined operation of the device and the system over a prolonged period of time.

EXAMPLE 2

An osmotic system 16 for housing in compartment 13 of osmotic device 10 is manufactured as follows: first, crystalline potassium chloride particles of 0.5 mm diameter are individually coated in a Wurster air suspension machine from a 5% solution of polymer in methylene chloride: methanol, (90: 10% by weight). The polymer is comprised of cellulose acetate Eastman Kodak, E-320 (30%), cellulose acetate E-398-10 (50%), and polyethylene glycol 650 (20%). The particles are coated to a thickness of 25 microns to achieve a polymer to drug ratio of about 12%. The encapsulated particles are next compounded into an osmotic system by blending them with a commercially available polymer ethylene-vinyl acetate acrylic acid. The polymer consists of 28% vinyl acetate, 1% acrylic acid and the balance ethylene. The compounding is effected in a mixer with gentle heat, 65°–70° C., for 10 to 15 minutes until the encapsulated particles of drug are surrounded by the polymer. Then, the product is removed from the mold, and while warm lightly pressed into a film that is cut into final osmotic systems. The osmotic systems contain 750 mg of potassium chloride.

Next, a semipermeable wall is applied around the systems in an Acella-Cota ® from a 5% solution of polymer in methylene chloride: methanol, (90:10 by weight). The wall forming polymer comprises cellulose acetate E-320, (80%) and polyethylene glycol-650, (20%). The osmotic devices have a semipermeable wall thickness of 250 microns (9.8 mil). A 9 mil aperture is drilled through the semipermeable wall to yield the completed devices.

EXAMPLE 3

In operation, the release of drug solute from a system as described above and considered with FIG. 4, and FIG. 5, is as follows: an osmotic drug solute, pilocarpine nitrate, present as a salt, in fine particle form is dispersed in a copolymer, such that every salt particle with radius $r_o$ is enclosed in its little depot or capsule with a membrane of thickness $h_o$. All the depots unite to form a matrix as seen in opened section in FIG. 4. The system is constructed with four solute impermeable walls, top, bottom, left and right. The system is exposed from the front and back. For calculation purposes, the ideal system will be assumed consisting of identical particles and homogeneous dispersion. Upon imbibition of water into the system, the depots at the exposed ends will imbibe water, swell and burst, and the water will move as a frount through the matrix from both ends, front and back. The time of bursting will be assumed as the releasing time since the permeation rate of the highly water soluble drug through the ruptured system, defined hereafter as the matrix, is large. Thus, the total mass of drug $M_t$ in the matrix is as follows:

$$M_t = N_t M_p \tag{1}$$

$$N_t = n_l \cdot n_w \cdot n_t \tag{2}$$

wherein:
 $n_l$ = number of particles of drug lined up in length l of the matrix;
 $n_w$ = number in W, FIG. 4;
 $n_t$ = number in t, FIG. 4;
Each of the quantities $n_l$, $n_w$ and $n_t$ can be expressed by an equation of the form (3).

$$n_l = \frac{l}{2(r_o + h_o)}, \tag{3}$$

It then follows from (1), (2), and (3) that:

$$M_t = \frac{l \cdot w \cdot t}{2^3 (r_o + h_o)^3} \times M_p \tag{4}$$

The total release time of the matrix is the time it takes for the water front to travel a distance of l/2, or the time it takes to burst nl/2 number of solute particles is expressed as follows:

$$t_t = \frac{l}{4(r_o + h_o)} t_b \times F \tag{5}$$

Since the depots are not independent, but are in the matrix, the time for bursting one deport in the matrix is $t_b \times F$, in which F is a factor accounting for the difference between a single and multiple depot system. When the particles are free, then F=1, since the depots are interlocked in the matrix, it is F is less than 1.

The zero order release rate for the system is calculated as follows from (4) and (5).

$$\text{Rate} = \frac{M_t}{t_t} = \frac{W \cdot t \cdot M_p}{2(r_o + h_o)^2 \cdot t_b \cdot F} \quad (6)$$

In order to arrive at the release rate from this kind of osmotic matrix, it is then necessary to derive the time $t_b$ needed to burst one depot capsule. In FIG. 5, a spherical osmotic capsule 23 is represented, with an osmotically active particle core 24, hereafter referred to with subscript p in the equations, enclosed in a semipermeable membrane 22, hereafter referred to with subscript c in the equations. When capsule 23 is submerged in water, it imbibes water by osmosis and the internal volume increases per unit time as described by equation 7.

$$\frac{dV}{dt} = k \cdot \frac{A}{h} (\Delta\pi - \Delta P) \quad (7)$$

wherein A is the membrane area, h is the thickness of the membrane, k is the permeation constant, $\Delta\pi$ is the osmotic pressure difference between the solution inside and outside the capsule, and $\Delta P$ is the hydrostatic pressure differences between the inside and the outside of the capsule.

The internal capsule volume expands from $V_o$, the volume at time zero, to $V_b$, the volume at bursting time, $t_b$. The bursting time is obtained from (7) and given by equation 8.

$$t_b = \int_{V_o}^{V_b} \frac{h \cdot dV}{k \cdot A(\Delta\pi - \Delta P)} \quad (8)$$

The quantities h, k, A, $\pi$, and P are all functions of volume. During the inital stages of swelling when the solution inside the capsule is saturated, equation 9 is as follows:

$$\Delta\pi = \pi^o \quad (9)$$

for the case where the osmotic pressure of the outside solution is negligible, and $\pi^o$ is the osmotic pressure inside the capsule up to a volume as expressed by equation 10.

$$V = V_o + \frac{M_P}{S} \quad (10)$$

wherein $M_p$ is the mass of the particle consisting essentially of an osmotically effective salt, and S is the solubility of the salt in water. For most applications, the volume at bursting $V_b$ is smaller than V given by equation 10. The quantities A, h, and V can conveniently be approximated as a function of the capsule radius as seen in equations 11 and 12.

$$A = 4\pi r^2 \quad (11)$$

$$V = (4/3)\pi r^3 \quad (12)$$

Thus, if the particle coating membrane deforms at a constant volume, it results in equation 13.

$$h = \frac{r_o^2}{r} h_o \quad (13)$$

wherein $r_o$ and $h_o$ are the particle radius and the membrane thickness at time zero.

At atmospheric conditions, P is equal to the internal pressure inside the membrane. In the practical applications, we will assume $h_o < < r_o$; and, for a thin walled sphere deformed in the elastic region, the inside pressure as a function of the radius is given by equation 14, where E is Young's modulus.

$$P = 2E \cdot h_o \cdot r_o \frac{(r - r_o)}{r^3} \quad (14)$$

and from equations (8), (9), (11), (12) and (13), equation 15 is obtained as follows:

$$t_b = \frac{r_o^2 \cdot h_o}{k} \int_{r_o}^{r_b} \frac{dr}{r^2(\pi^o - P)} \quad (15)$$

$$P << \pi^o \quad (16)$$

For particles which are encapsulated in a thin membrane, the elastic back-pressure of the capsule is negligible and equation (16) is mathametically reasonable, as will be demonstrated with the following presentation.

The maximum expected elastic back-pressure at bursting for a ratio of membrane to particle weight is estimated, and for a thin walled capsule, the mass of the capsule is given by equation 17, where $\rho_c$ is the density of the membrane.

$$M_c = 4\pi r_o^2 \cdot h_o \rho_c \quad (17)$$

The mass of particle 23, (FIG. 5), is given by equation 18, wherein $\rho p$ is the density of particle 23.

$$M_p = \frac{4}{3} r_o^3 \cdot p \quad (18)$$

with the ratio of the particle 23 to the membrane coating weight 24 given by equation (17) and equation (18) as follows:

$$\frac{M_p}{M_c} = \frac{r_o \cdot p_p}{3 \cdot h_o \cdot c} \quad (19)$$

for $\rho_p \simeq \rho_c$ equation 21 results.

$$\frac{M_p}{M_c} = \frac{r_o}{3 h_o} \quad (20)$$

and, in the range of interest where $$M_c/M_p = 0.3 \quad (21)$$

the ratio presents itself in equation 22.

$$h_o = r_o/10 \quad (22)$$

The bursting pressure of a spherical capsule or depot is given by equation 23.

$$P_b = 2 \cdot \sigma_t \cdot \frac{h_f}{r_f} \quad (23)$$

wherein $\sigma$ is the tensile strength, $h_f$ is the final thickness and $r_f$ is the final radius. The burst pressure in terms of elongation (El) of the membrane 23, and the original dimensions is given by equation 24.

$$P_f = 2 \cdot \sigma_t \cdot \frac{h_o}{r_o} \cdot \frac{1}{(1 + El)^3} \qquad (24)$$

which for ethylene-vinyl acetate copolymer having an vinyl acetate content of 28% is $\sqrt{t}=675$ psi and $E_l=1400$ percent. From equation (24), the burst pressure is about $2.7 \cdot 10^{-3}$ atm and it is negligible compared to the osmotic pressure of the particle 21 which is about 50 atm.

Thus, assuming (16) the brusting time from (15) is then given by equations 25, 26 and 27 as follows:

$$t_b = \frac{r_o^2 \cdot h_o}{k \cdot \pi^o} \int_{r_o}^{r_b} \frac{dr}{r^2} = \frac{r_o^2 \cdot h_o}{k \cdot \pi^o} \left(\frac{-1}{r}\right)\bigg|_{r_o}^{r_b} \qquad (25)$$

$$t_b = \frac{r_o^2 \cdot h_o}{k\pi^o} \left( \frac{1}{r_o} - \frac{1}{r_o(1 + El)} \right) \qquad (26)$$

$$t_b = \frac{h_o \cdot r_o}{k\pi^o} \cdot \frac{El}{1 + El} \qquad (27)$$

Using equation (20), it is then convenient to express the bursting time in terms of the particle to the membrane coating ratio as follows:

$$t_b = \frac{r_o^2}{3\pi^o \cdot k} \cdot \frac{M_c}{M_p} \cdot \frac{E}{(1 + El)} \qquad (28)$$

which can also be written as (29) where f(El) is a junction of elongation $$tl = \frac{r_o^2}{3 \cdot \pi o \cdot k} \cdot \frac{M_c}{M_p} \cdot f(El) \qquad (29)$$

Equation (28) gives the bursting time for what can be called a soft capsule, or soft depot, in which the hydrostatic pressure is low compared to the osmotic pressure for a combination of two reasons, (1) the osmotic pressure of the particle is high, and (2) the membrane forming the wall of the capsule, or encapsulating the particle as a depot has a low Young's modulus. In a hard capsule, it is expected that $t_b$ is proportional to the square of $M_c/M_p$ because the coating retards water influx, and increased coating retards water influx because of pressure buildup. The release rate from such an osmotic matrix follows then from equations (6) and (28).

$$\text{Rate} = \frac{3W \cdot t}{2(r_o + h_o)^2 \cdot r^2} \cdot \frac{k\pi^o}{F \cdot f(El)} \cdot \frac{M_p}{M_c} \cdot M_p \qquad (30)$$

In the last equation, the quantity [F·f(El)] can be interpreted as the effective elongation in the matrix, at which rupture occurs. An estimate of this number can be obtained as the ratio of wet to dry thickness of the distended part of the matrix. The last equation can further be approximated by substituting (18) and $p_p=1$ gr/ml into (30) and assuming $h_o \ll r_o$, with the e $$\text{Rate} = \frac{6.28}{F \cdot f(El)} \cdot \frac{w \cdot t}{r_o} \cdot k^o\pi \cdot \frac{M_p}{M_c} \qquad (31)$$

Figure 6:
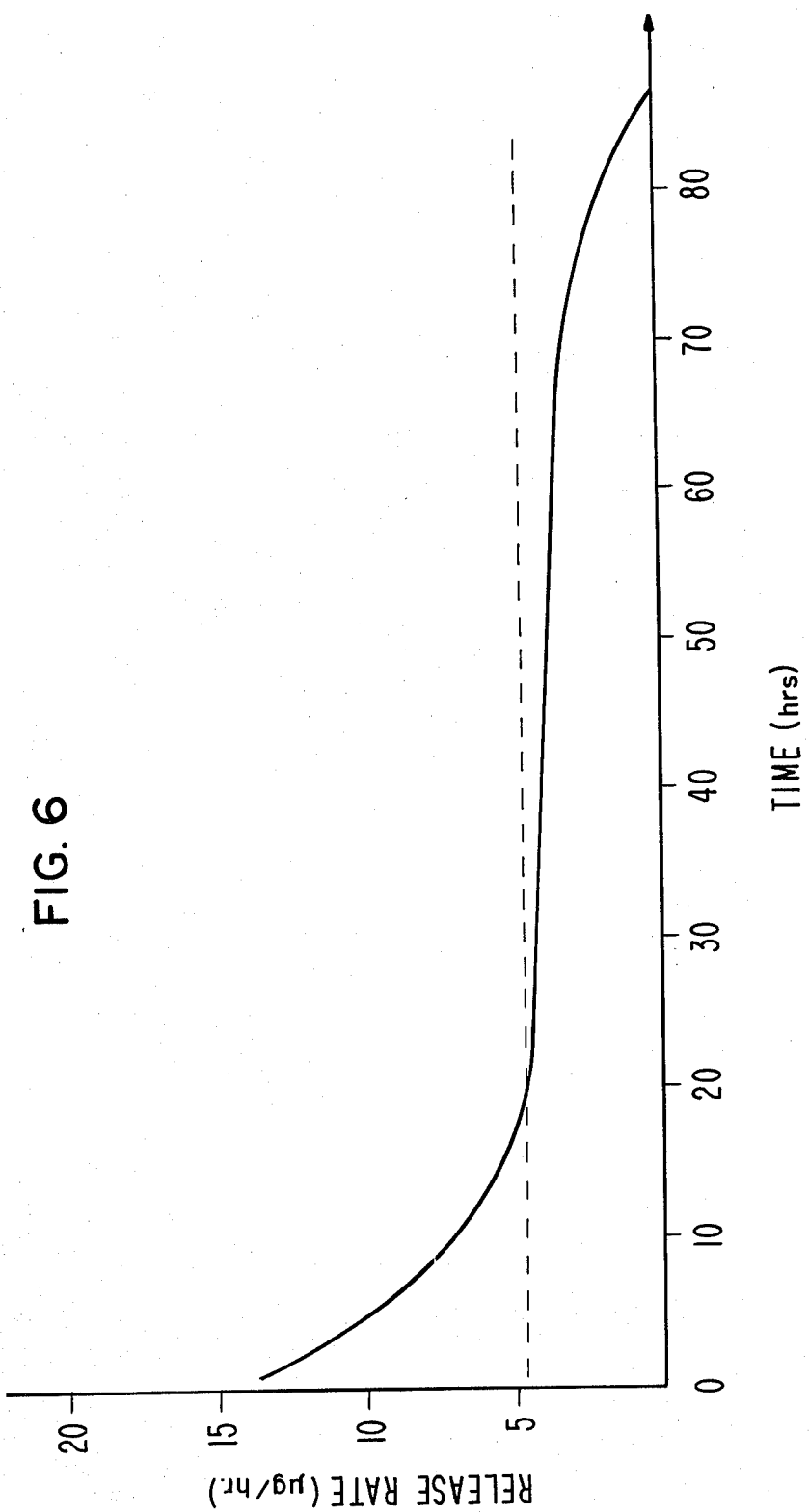

Thus, for a system of pilocarpine nitrate having a loading of 70% in ethylene-vinyl acetate copolymer having an acetyl content of 40%, $M_c/M_p=3/7$, with a particle size $2r_o=10$ g$=10.10^{-4}$ cm, a core thickness t=10 mil=25.4 $10^{-3}$ cm, a core width W=0.5 cm, and a water permeability $$k\pi^o = \frac{10^{-4} \text{ cc} \cdot \text{mil}}{\text{cm}^2 \cdot \text{hr}}, \qquad (32)$$

with $t_b=0.14$ (fE$_l$) hr, and the rate estimated as Rate$=94/F\cdot E$ ($\mu$g/hr); where in experiments it was found that swelling of the matrix represented by F·(fE$_l$) is about 2, the expected rate is 47 $\mu$g/hr. The release rate for this system was measured and set forth in FIG. 6. In FIG. 6, the dashed lines is the theoretical rate of release from the system, and the continuous line is the measured rate of release. The data indicates experimental verification of the calculated result.

While the invention has been illustrated and described in detail, it is not intended to be limited to the details disclosed, since various modifications and changes can be made without departing in any way from the spirit of the present invention.

What is claimed is:

1. An osmotic device for delivering an agent to an environment of use, said device comprising:
    (a) a shaped wall formed of a material that is permeable to the passage of an exterior fluid present in the environment of use, and substantially impermeable to the passage of agent, the wall surrounding and forming;
    (b) a compartment;
    (c) an osmotic system in the compartment, which system comprises a body formed of depots of agent osmotic solute dispersed in a polymer that is impermeable to the passage of solute and permeable to the passage of fluid, with the depots surrounded substantially individually by a layer of polymer; and
    (d) a passageway in the wall communicating with the compartment and the exterior of the device for delivering agent from the device to the environment of use.

2. The osmotic device for delivering agent according to claim 1 wherein, when in operation with the osmotic device is in a fluid environment of use, fluid from the environment is imbibed through the wall into the compartment in a tendency towards osmotic equilibrium at a rate determined by the permeability of the wall of the device and osmotic pressure gradient across said wall, thereby forming a solution containing agent that is released by the osmotic device through the passageway at a controlled rate over time.

3. The osmotic device for delivering agent according to claim 1, wherein, when the device is in operation in a fluid environment, the osmotic system imbibes fluid from the compartment through the polymer of the system into the depots to continuously dissolve the agent solute, and form a solution that generates a hydrostatic pressure in the depots, which pressure is applied against the polymer layer of the depots, thereby forming apertures and releasing the agent from the system into the compartment, with the device delivering the agent from the compartment through the passageway to the environment at a controlled rate over time.

4. The osmotic device for delivering the agent according to claim 1 wherein the agent is delivered by the combined operations of the osmotic device and the osmotic system.

5. The osmotic device for delivering the agent according to claim 1 wherein the agent is an osmotically effective drug solute.

6. The osmotic device for delivering the agent according to claim 1 wherein the device is sized and adapted for delivering the agent in the gastrointestinal tract.

7. The osmotic device for delivering the agent according to claim 1 wherein the wall of the device is formed of a member selected from the group consisting of cellulose acylate, cellulose diacylate, cellulose triacylate, cellulose acetate, cellulose diacetate, and cellulose triacetate.

8. The osmotic device for delivering the agent according to claim 1 wherein the polymer forming the osmotic system in the compartment is a member selected from the group consisting of ethylene-vinyl ester copolymer, ethylene-vinyl acetate copolymer, poly(ethylene), and ethylene-propylene copolymer, polyurethane and plasticized cellulose ester, and plasticized cellulose ether.

9. The osmotic device for delivering the agent according to claim 1 wherein the osmotically effective agent solute in the osmotic system is a member selected from the group consisting of pesticide, herbicide, biocide, algicide, rodenticide, insecticide, and a drug.

* * * * *